United States Patent
Guloy, Jr. et al.

(10) Patent No.: US 9,707,086 B2
(45) Date of Patent: Jul. 18, 2017

(54) TOTAL KNEE ARTHROPLASTY METHODS, SYSTEMS, AND INSTRUMENTS

(71) Applicant: Orthopaedic International, Inc., Cabuyao, Laguna (PH)

(72) Inventors: Ilustre I. Guloy, Jr., Laguna (PH); Ramon B. Gustilo, Eden Prairie, MN (US); Jesus L. Muñoz, Imus (PH); Paul Cesar N. San Pedro, Quezon (PH); Jude L. Sasing, Quezon (PH)

(73) Assignee: Orthopaedic International, Inc., Cabuyao, Laguna (PH)

( * ) Notice: Subject to any disclaimer, the term of this patent is extended or adjusted under 35 U.S.C. 154(b) by 497 days.

(21) Appl. No.: 14/175,208

(22) Filed: Feb. 7, 2014

(65) Prior Publication Data

US 2014/0228851 A1 Aug. 14, 2014

Related U.S. Application Data

(60) Provisional application No. 61/762,492, filed on Feb. 8, 2013, provisional application No. 61/904,083, filed
(Continued)

(51) Int. Cl.
*A61F 2/46* (2006.01)
*A61F 2/38* (2006.01)
(Continued)

(52) U.S. Cl.
CPC .......... *A61F 2/3859* (2013.01); *A61B 17/155* (2013.01); *A61B 17/157* (2013.01);
(Continued)

(58) Field of Classification Search
CPC .................................................. A61F 2/4657
(Continued)

(56) References Cited

U.S. PATENT DOCUMENTS 4,759,350 A * 7/1988 Dunn ................... A61B 17/154
606/82
4,944,760 A * 7/1990 Kenna ....................... A61F 2/38
128/898
(Continued)

FOREIGN PATENT DOCUMENTS

EP  0 677 274  1/2003
EP  2 083 714  12/2011

OTHER PUBLICATIONS

Zimmer MIS Multi-Reference 4-in-1 Femoral Instrumentation Surgical Technique, Copyright 2009 Zimmer Inc.
(Continued)

*Primary Examiner* — David Bates
(74) *Attorney, Agent, or Firm* — Kagan Binder, PLLC

(57) ABSTRACT

A method of performing a total knee arthroplasty including the steps of inserting a first pin into the distal femur and through the knee center, locating the femoral mechanical axis, inserting at least one additional pin into the distal femur, locating the tibial mechanical axis, sizing the femur and applying a femoral cutting block having at least one cutting guide to an end of the femur, positioning a tibial cutting block having a least one cutting guide in a cutting position relative to the tibia, aligning the femoral cutting block relative to the tibial cutting block, aligning the femur relative to the tibia, cutting the femur using the at least one femoral cutting guide, cutting the tibia using the at least one tibial cutting guide, removing the femoral and tibial cutting blocks, and positioning permanent femoral and tibial components on the cut portions of the femur and tibia, respectively.

20 Claims, 19 Drawing Sheets

Related U.S. Application Data on Nov. 14, 2013, provisional application No. 61/904,086, filed on Nov. 14, 2013, provisional application No. 61/904,099, filed on Nov. 14, 2013.

(51) Int. Cl.
*A61B 17/17* (2006.01)
*A61B 17/15* (2006.01)

(52) U.S. Cl.
CPC .......... *A61B 17/1764* (2013.01); *A61F 2/389* (2013.01); *A61F 2/3877* (2013.01); *A61F 2/4657* (2013.01); *A61F 2/38* (2013.01); *A61F 2002/4668* (2013.01)

(58) Field of Classification Search
USPC ...................................................... 606/88, 90
See application file for complete search history.

(56) References Cited

U.S. PATENT DOCUMENTS

| | | | |
|---|---|---|---|
| 5,330,534 A | 7/1994 | Herrington et al. | |
| 5,358,527 A | 10/1994 | Forte | |
| 5,520,694 A | 5/1996 | Dance et al. | |
| 5,601,566 A | 2/1997 | Dance et al. | |
| 5,611,353 A | 3/1997 | Dance et al. | |
| 5,649,929 A * | 7/1997 | Callaway | A61B 17/025 606/87 |
| 5,690,638 A | 11/1997 | Dance et al. | |
| 5,871,540 A | 2/1999 | Weissman et al. | |
| 6,478,799 B1 | 11/2002 | Williamson | |
| 6,928,742 B2 | 8/2005 | Broers et al. | |
| 7,331,932 B2 | 2/2008 | Leitner | |
| 7,427,272 B2 | 9/2008 | Richard et al. | |
| 7,708,740 B1 | 5/2010 | Bonutti | |
| 7,805,852 B2 | 10/2010 | Collette | |
| 7,875,081 B2 | 1/2011 | Lipman et al. | |
| 7,892,240 B2 | 2/2011 | Claypool et al. | |
| 7,967,822 B2 | 6/2011 | Haines et al. | |
| 8,092,546 B2 | 1/2012 | Coon et al. | |
| 8,118,811 B2 | 2/2012 | Coon et al. | |
| 8,172,842 B2 | 5/2012 | Sasing | |
| 8,308,730 B2 | 11/2012 | Radermacher et al. | |
| 8,409,210 B2 | 4/2013 | Bhatnagar et al. | |
| 2005/0070897 A1 | 3/2005 | Petersen | |
| 2006/0184173 A1 | 8/2006 | Collazo | |
| 2008/0195110 A1 | 8/2008 | Plassy et al. | |
| 2008/0312659 A1 * | 12/2008 | Metzger | A61B 17/154 606/87 |
| 2009/0088754 A1 | 4/2009 | Aker et al. | |
| 2009/0125029 A1 | 5/2009 | Seo et al. | |
| 2009/0222014 A1 | 9/2009 | Bojarski et al. | |
| 2009/0228111 A1 | 9/2009 | Otto | |
| 2010/0191298 A1 | 7/2010 | Earl et al. | |
| 2011/0144704 A1 | 6/2011 | Switzer | |
| 2011/0305379 A1 | 12/2011 | Mahfouz | |
| 2012/0029581 A1 | 2/2012 | Kanekasu | |
| 2012/0232671 A1 | 9/2012 | Bojarski et al. | |

OTHER PUBLICATIONS

EP 14748488 Supplemental European Search Reported dated Jan. 2, 2016.

* cited by examiner

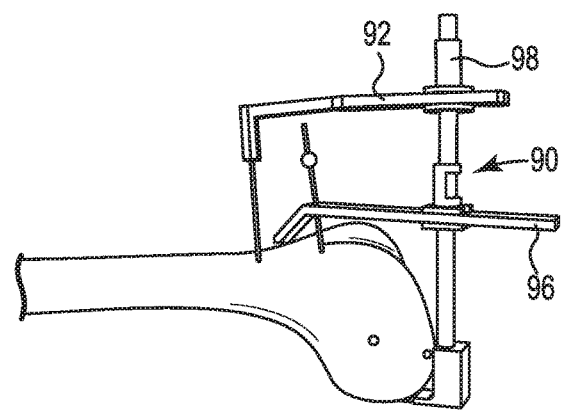
Fig. 15
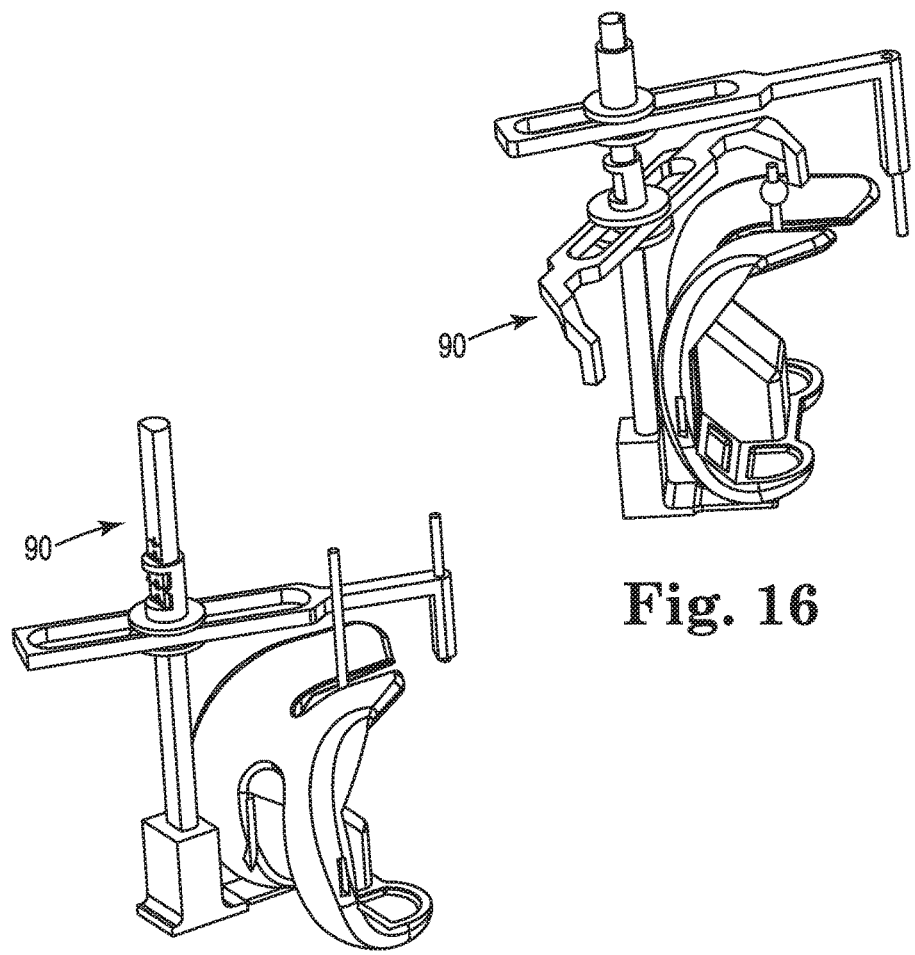
Fig. 16
Fig. 17

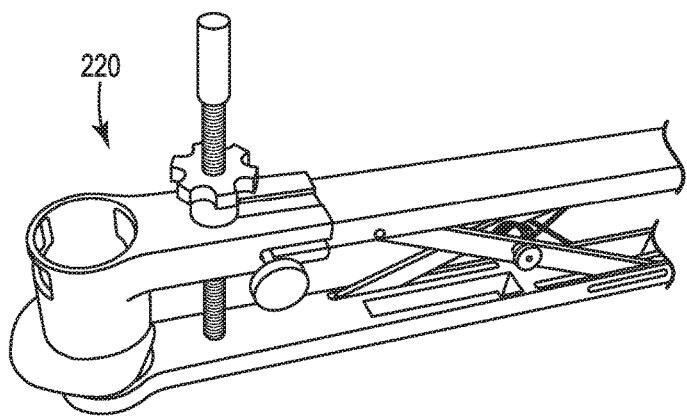
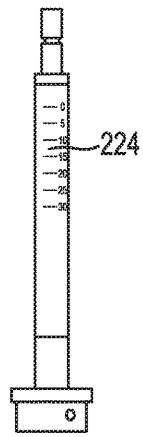
Fig. 43    Fig. 44
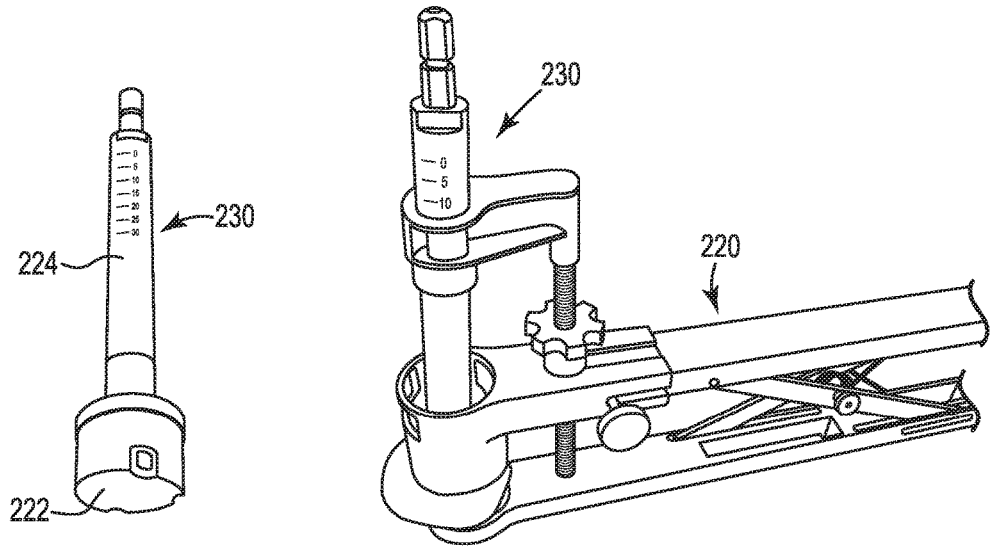
Fig. 45    Fig. 46

TOTAL KNEE ARTHROPLASTY METHODS, SYSTEMS, AND INSTRUMENTS

CROSS-REFERENCE TO RELATED APPLICATIONS

This application claims the benefit of U.S. Provisional Patent Application No. 61/762,492, filed Feb. 8, 2013 entitled "INSTRUMENT FOR LOCATING THE FEMORAL MECHANICAL AXIS", U.S. Provisional Patent Application No. 61/904,083, filed Nov. 14, 2013 entitled "INSTRUMENTS AND METHODS FOR LOCATING A FEMORAL MECHANICAL AXIS", U.S. Provisional Patent Application No. 61/904,086, filed Nov. 14, 2013 entitled "TOTAL KNEE ARTHROPLASTY METHODS, SYSTEMS, AND INSTRUMENTS", and U.S. Provisional Patent Application No. 61/904,099, filed Nov. 14, 2013 entitled "TOTAL KNEE ARTHROPLASTY METHODS, SYSTEMS, AND INSTRUMENTS", which applications are incorporated herein by reference in their entireties.

TECHNICAL FIELD

The invention relates to methods, systems, and instruments used for total knee arthroplasty (TKA), including surgical techniques. In particular, the TKA techniques of the invention utilize instruments that do not violate the intramedullary canals of the femur and tibia and that allow multiple bone cuts with minimal reorientation of cutting guides.

BACKGROUND

In total knee arthroplasty procedures, a number of instruments and techniques can be utilized. In many procedures, the surgery begins with exposing the ends of the bones that make up the knee, including the femur, the tibia, and the patella. An elongated drill hole is then made in the distal femur, and an intramedullary rod is inserted into the hole. A first cutting guide is then inserted onto this rod and positioned in the correct anteroposterior and rotational orientation, and then the anterior cortex is cut with a saw. The first cutting guide is then removed and replaced with a second cutting guide that is used to cut the distal femur in the correct valgus angle. The second cutting guide is then removed, along with the intramedullary rod. The femur can then be measured to determine the size of the femoral component that will be used.

After sizing the femoral component, yet another cutting guide (i.e., a third cutting guide) is positioned on the cut surfaces and pinned or secured in place. Anterior, posterior, and chamfer cuts are made using a saw as guided by the third cutting guide, and then the third cutting guide is removed. A fourth cutting guide is then positioned and pinned on the cut surfaces to make a cut know as the "box cut". After this cut is done, the fourth cutting guide is removed. A trial femoral component is then positioned relative to the cut surfaces to check for proper fit relative to the bone.

The tibia is then subluxed forward so that an extramedullary guide can be positioned relative to it. In particular, this extramedullary guide is positioned so that it can attach from the tibial plateau on its proximal part to the ankle at its distal part. At this point, a fifth cutting guide can be positioned relative to the tibia and pinned or secured in place. Alternatively, a hole can be drilled into the tibia in a similar manner to the technique used to drill into the femur so that another intramedullary rod can be inserted. The fifth cutting guide can then be positioned on this rod. In either case, once the fifth cutting guide is in its desired location, the tibia can be cut and the guide can be removed. The proximal tibia is generally prepared using a short punch that will make a tubular hole in the bone, and a stem of a trial tibial component can then be inserted into the tubular hole.

Once the trial femoral and tibial components are placed in their desired locations, the relationship between the femur and tibia is tested and corrected so that they are balanced in the medial and lateral sides during extension and flexion. The whole lower extremity axis is also checked to be sure that it is straight. Tight structures and/or incorrect bone cuts may make the system unbalanced and/or make the axis incorrectly aligned, wherein either or both of these issues will require correction. In particular, if the structures are too tight, they can be released. If the bone cuts made were too small or thin, they can be cut again using the previous sequence of the use of cutting guides and cuts. If the bone cuts are too large or thick, appropriate inserts can be added to the bone to make it the desired size and shape. All of these corrections or adjustments require extra steps that are inconvenient and may ultimately result in a less successful surgical outcome.

As set out above, the successful outcome of a total knee arthroplasty includes achieving accurate bone cuts and adequate ligament balancing. In particular, the bone cuts must be accurately made in relation to the mechanical axis of the femur, which can be difficult to identify because it extends from the center of the femoral head to the center of the knee joint, wherein the femoral head cannot be visualized during total knee surgery. The most widely used method of locating the mechanical axis is with a rod that is positioned in the femoral medullary canal. The mechanical axis is then estimated to be positioned approximately 6 degrees medially from the axis of the rod. Although this method can be easy to implement, it is not necessarily accurate due to variations in the anatomy of the femur and due to the play between the rod and the medullary canal in which it is positioned. This method also cannot determine the direction of the mechanical axis when viewed in the sagittal plane. Furthermore, this method requires the medullary canal to be violated, which can potentially lead to undesirable blood loss and possible complications. Violating the canal can also potentially lead to fat embolism or activation of coagulation. Another way of locating the mechanical axis is by using computerized navigation equipment to identify bony landmarks and relate them to the motion of the femur to locate the mechanical axis. However, such equipment is often relatively expensive, and can be cumbersome to use in surgery.

After the femur and tibia are balanced and their alignment is straight, the patella can be resurfaced and/or the knee can be moved through its range of motion to check for correct patella tracking. In cases where the patella is going to be resurfaced, the patella is everted when the knee is straight. The patellar thickness can be measured, such as with a caliper, and then a patella cutting guide is applied to the patella to cut the amount of patella that will later be replaced by plastic. Once the patella is cut, a trial plastic component can be positioned relative to the cut area and the whole knee is then checked for balance, alignment, and patellar movement or tracking. After this process is complete, the trial components are removed, the bone ends are cleaned and dried, bone cement is applied in the appropriate locations, and the final components are placed in their desired locations. Balance, alignment, and patellar tracking are checked again, the knee is closed, and the surgery is considered to be complete.

Although many of the described processes work reasonably well, there is a need to provide systems and methods for use in total knee arthroplasty that are less invasive, more accurate, and more simple, both for locating the femoral mechanical axis accurately in both the coronal and sagittal planes and for making accurate bone cuts using more simplified cutting guides.

SUMMARY

The invention described herein relates to a method of performing a total knee arthroplasty, which offers a number of features that contribute to successful outcomes. In embodiments of the invention, methods, instruments, and devices are provided for locating the femoral head without the use of radiation or computer navigation and in which the intramedullary canals of the femur and tibia are not violated. In embodiments of the invention, the initial soft tissue balance is done first to emphasize the soft tissue requirements of total knee arthroplasty (i.e., the importance of balancing the ligaments that hold the bones together). That is, by relating the femur to the tibia prior to cutting any bones, less adjustment of the ligaments is needed. In embodiments of the invention, all of the cuts of the femur and tibia are performed without changing the position of the knee and/or without removal, reorientation, or replacement of cutting jigs.

In an embodiment of the invention, a method of performing total knee arthroplasty is performed that includes the steps of exposing a knee of a patient, identifying the center of the knee, inserting a first pin into an anterior aspect of a distal femur and through the center of the knee, locating a femoral mechanical axis with reference to the center of the knee, inserting at least one additional pin into the anterior aspect of the distal femur, the axis of said at least one additional pin intersecting with and perpendicular to the femoral mechanical axis, locating a tibial mechanical axis, sizing the femur and applying a femoral cutting block to a distal end of the femur, wherein the femoral cutting block comprises at least one femoral cutting guide, positioning a tibial cutting block in a cutting position relative to a proximal end of the tibia, wherein the tibial cutting block comprises at least one tibial cutting guide, aligning the femoral cutting block relative to the tibial cutting block, aligning the femur relative to the tibia, cutting the femur through the at least one femoral cutting guide, cutting the tibia through the at least one tibial cutting guide, removing the femoral and tibial cutting block, and positioning a permanent femoral knee implant component on the cut portion of the femur and positioning a permanent tibial knee implant component on the cut portion of the tibia. The femoral and tibial cutting guides each can include slots through the femoral and tibial cutting blocks, respectively, wherein these cutting guides are positioned in locations that allow for all of the cuts to be performed of the femur and tibia that are desired for accepting their respective permanent knee implant components.

In accordance with the method described above, the step of aligning the tibia relative to the femur may include positioning a jack-up device between the tibial spine and the intercondylar notch and activating the jack-up device to orient the femur in a desired external and internal rotation relative to the tibia. The femoral and tibial cutting blocks can remain in their respective positions relative to each other and relative to their respective femur and tibia during the positioning and activating of the jack-up device. In addition, the step of locating the femoral mechanical axis may include using a mechanical axis finder that does not require violation of the intramedullary canal of the femur.

The method described above may further include a step of resurfacing the patella of the patient after positioning the permanent femoral and tibial knee implant components relative to the femur and tibia, respectively. In addition, the method may further include a step of positioning at least one trial femoral knee implant component and at least one tibial knee implant component on the cut portion of the femur and the cut portion of the tibia, respectively, and then removing the trial femoral and tibial knee implant components prior to the step of positioning permanent femoral and tibial knee implant components. The method may also include a step of performing soft tissue release after the step of locating the tibial mechanical axis, and/or the step of aligning the tibia relative to the femur may include attaching the femoral cutting block to the tibial cutting block.

BRIEF DESCRIPTION OF THE DRAWINGS

The present invention will be further explained with reference to the appended Figures, wherein like structure is referred to by like numerals throughout the several views, and wherein:

FIG. 15 is a perspective view of a femoral sizer positioned relative to a representative femur that has multiple extending pins;

FIG. 16 is a perspective view of a femoral sizer positioned relative to a representative portion of a knee implant;

FIG. 17 is another perspective view of a femoral sizer positioned relative to a representative portion of a knee implant;

FIG. 43 is a perspective view of a patellar clamp of the invention;

FIG. 44 is a perspective view of a reamer shaft for use with the patellar clamp of FIG. 43;

FIG. 45 is a perspective view of a reamer shaft with an attached measuring sleeve;

FIG. 46 is a perspective view of a reamer shaft positioned relative to a patellar clamp;

DETAILED DESCRIPTION

Figure 1:
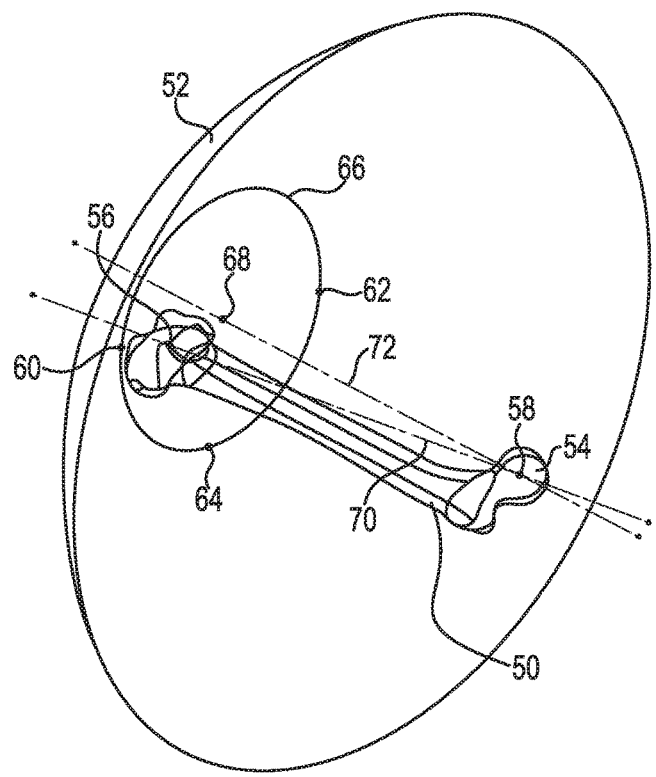
FIG. 1 is a schematic diagram of a representative sphere in relation to a femur, in accordance with the invention.

There are numerous total knee arthroplasty systems that have been used with reasonable success, wherein each system includes different sets of instrumentation and different techniques that accompany each set. Several issues that are encountered when using these systems are not present using the methods, systems, and instruments of the invention, which are first described in general below, and then with respect to particular embodiments of the invention.

A primary goal of any total knee arthroplasty surgery is to properly align the lower limb. This alignment is guided by three points, which include (1) the center of the femoral head; (2) the center of the knee; and (3) the center of the ankle. Because the center of the knee and the center of the ankle are accessible during surgery, it is relatively straightforward to find these points. However, the femoral head is deep in the hip and is outside the surgical field. Many systems that have been developed use guide rods inserted in the femoral canal and use these rods as reference structures that are used to arrive at an average value in degrees that will be assumed to point to the femoral head. Some systems also use preoperative x-rays to locate the femoral head and put a physical marker that the surgeon can palpate during surgery. Yet other systems use expensive computer navigation to locate the femoral head. However, in accordance with the invention, embodiments of the systems described herein use a mechanical axis finder that does not require radiation nor expensive equipment.

A successful total knee arthroplasty also requires that the ligaments that hold the bones together are balanced, which, in accordance with the present invention, is performed prior to cutting any of the bones. That is, once the knee ligaments are initially balanced, the bone cutting guides of the invention are positioned onto their respective surfaces, and then the cutting is performed. Further in accordance with embodiments of the invention, all bone cuts are made with the bones in one position, unlike in other systems where the knee is in one position when cutting the femur and in another position when cutting the tibia. Finally, the cuts made using the devices and methods of the invention will be more accurate, thereby minimizing any possible complications that can arise from cutting more bone than necessary.

Referring now to the Figures, wherein the components are labeled with like numerals throughout the several Figures, a number of steps are for a total knee arthroplasty in accordance with the invention are illustrated and described. In preparation for the surgery, appropriate surgical drapes and a foot/ankle positioner are used to position the knee in a desired configuration for access by the surgeon, and then the surgical procedure can be performed.

To begin the surgery, the knee of a patient is exposed. In this step, a medial parapatellar incision is used to expose the knee so that the anterior cruciate ligament (ACL) and the medial collateral ligament (MCL) and both menisci can be removed. Any osteophyte that can be accessed is also removed. The patella is moved to the side.

Next, the femoral mechanical axis is located, which can be performed using various methods, wherein one method of the invention includes using the mechanical axis finder of U.S. Provisional Application No. 61/762,492, filed Feb. 8, 2013, the contents of which are incorporated herein by reference. In general, locating the mechanical axis using this method includes the determination of certain points in space relative to the femur of the patient, such as is illustrated in FIGS. 1-6. With initial reference to FIG. 1, a schematic diagram of a femur 50 and a portion of a sphere 52 is shown. The sphere 52 and the femur 50 are positioned so that a center of the femoral head 54 coincides with a center 58 of sphere 52. Furthermore, the center of the knee 56 is on the surface of the sphere 52. Thus, sphere 52 has a radius equal to the distance from the center of the femoral head 54 to the center of the knee 56.

In accordance with the present invention, issues that are commonly encountered when attempting to locate the mechanical axis of a femur can be solved by finding a line that passes through the center 58 of sphere 52 using points on the surface of the sphere, such as first point 60, second point 62, and third point 64, as are shown in FIG. 1. Locating such a line can be accomplished using devices and/or methods of the present invention. Further in accordance with the invention, the physical movement of a knee is presumed to pivot three-dimensionally around the center of the femoral head. Thus, the center of the knee 56 will trace the surface of sphere 52 when the knee is moved about, whereby it moves through points 60, 62, and 64.

It can be shown that for any given sphere, a line passing through the center of, and perpendicular to the plane of, a circle defined by at least three points on the sphere will pass through the center of the sphere. As applied to the present invention, points 60, 62, and 64 are on the surface of sphere 52 and are used to define a circle 66 with center 68. In order to locate the mechanical axis 70 for a particular femur, the center of the knee 56 is moved to an arbitrary point in space that can be made to correspond to first point 60. The center of the knee 56 is then moved to second point 62, and finally to third point 64. These points 60, 62, and 64 are used to define circle 66, and then point 68 can then be identified as the center of this circle. After all of these points are identified and/or located, the axis 72 can be identified, which is perpendicular to the plane containing circle 66 and passing through the center 68 of circle 66. By moving the center of the knee 56 to coincide with axis 72, the mechanical axis 70 of the femur 50 becomes collinear with an axis 72, allowing it to be located. Devices and methods of the invention that can be used to identify points 60, 62, 64, and 68, and axis 72 in relation to a femur, and hence able to locate the femoral mechanical axis, are described in the succeeding paragraphs.

Figure 2:
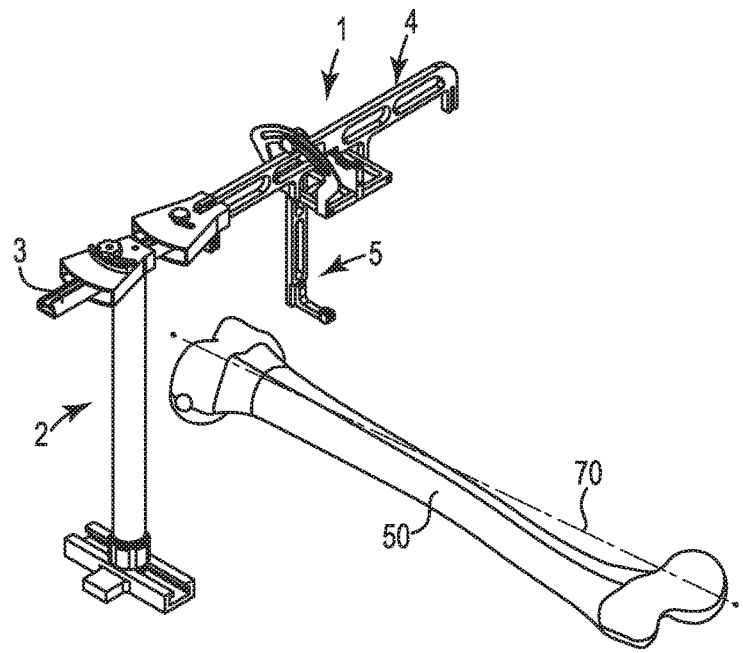
FIG. 2 is a perspective view of an embodiment of a mechanical axis finder of the invention, positioned relative to a femur.

Referring now to FIG. 2, an embodiment of a mechanical axis finder 1 of the invention is illustrated, which generally includes a base 2, an extension arm 3, a swiveling arm 4, and a locating arm 5. A representative or exemplary femur 50 of a patient is also shown adjacent to the mechanical axis finder 1. Base 2 is attachable to an operating table by clamping it to the side rail of the table or by using any other attachment structure or structures that provide for secure engagement between the mechanical axis finder and the table. In an exemplary method of using a mechanical axis finder of the type illustrated in FIG. 2, after the knee joint is exposed, the center of the knee 56 is identified by the surgeon in the coronal and sagittal planes. A knee center locator device can be used for locating this knee center, if desired. It should be noted that the "sagittal plane" being referred to in this and in the succeeding paragraphs is a plane parallel to the anatomical sagittal plane and passing through the center of the knee.

Figure 3:
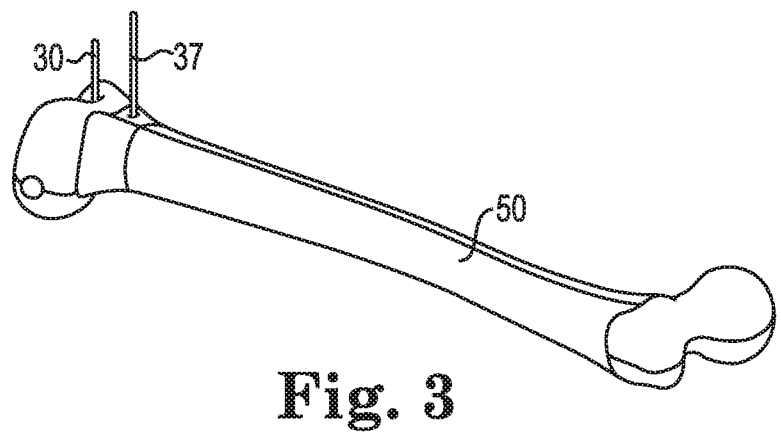
FIG. 3 is a perspective view of guide pins positioned in representative locations in a femur.

Once the center of the knee 56 is located, a pin 30 (which may optionally include a bead, a band, or another locating feature) is inserted into the anterior aspect of the distal femur, along the sagittal plane approximately perpendicular to the femoral anatomical axis and going through the center of the knee 56, as shown in FIG. 3. The pin 30 is inserted so that its locating feature is at a predetermined distance from the center of the knee 56. This position of locating feature and the center of the femoral head 54 are two points used to define the "approximate mechanical axis" of the femur, which extends from the center of the femoral head 54 to the center of the locating feature.

The mechanical axis finder 1 includes a number of components and devices that are moveable and/or lockable relative to each other in order to locate the specific points described above. Once these steps have been performed, the locating feature of the pin 30 is engaged with a bracket and the femur is oriented so that a guide pin 37 can be drilled into femur 50 at a predetermined distance/location relative to the pin 30, as is illustrated in FIG. 3, in such a way that it compensates for the angle between the true mechanical axis 70 and the approximate mechanical axis. Thus, when pin 37 is drilled into femur 50, it is perpendicular to axis 70 of FIGS. 1 and 2.

Figure 4:
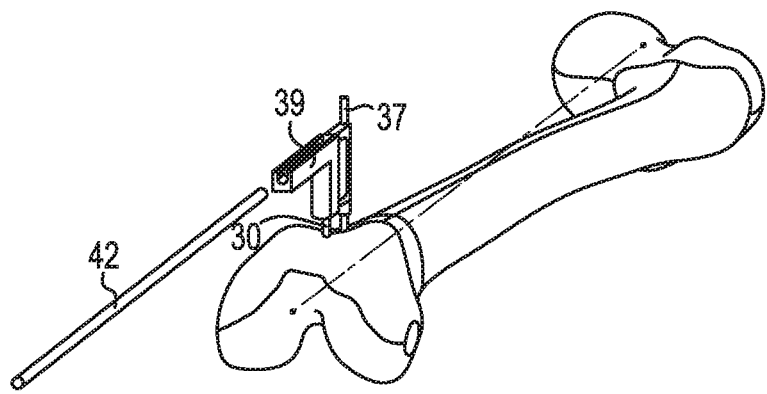
FIG. 4 is a perspective view of an alignment guide positioned relative to a femur.
Figure 5:
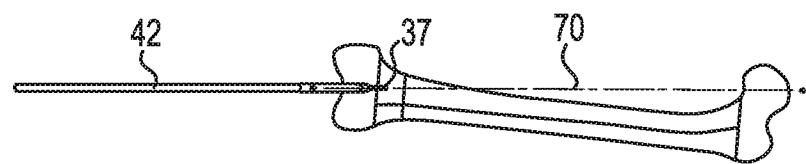
FIG. 5 is a top view of a femur with an alignment rod positioned parallel to the mechanical axis when viewed in the coronal plane.
Figure 6:
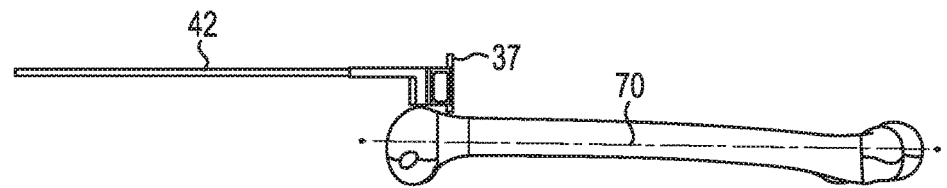
FIG. 6 is a side view of a femur with an alignment rod positioned in line with the mechanical axis when viewed in the sagittal plane.

The mechanical axis finder 1 is then removed from the patient while leaving guide pins 30 and 37 positioned in their respective locations in the femur 50, as shown in FIG. 3. A rod alignment guide 39 is then placed over pins 30 and 37, as shown in FIG. 4. In particular, rod alignment guide 39 includes a guide hole that is slideable over pin 37 and guide slot that is slideable over pin 30. Finally, an alignment rod 42 is placed inside a guide hole of alignment guide 39. Alignment rod 42 will be collinear with the mechanical axis 70 when viewed in the coronal plane and parallel to the mechanical axis 70 when viewed in the sagittal plane, as shown in FIGS. 5 and 6. Guide pin 37 will be perpendicular to the mechanical axis 70 when viewed in the sagittal plane. The line connecting the locating feature and the axis of guide pin 37 will be collinear with the mechanical axis when viewed in the coronal plane.

Figure 7:
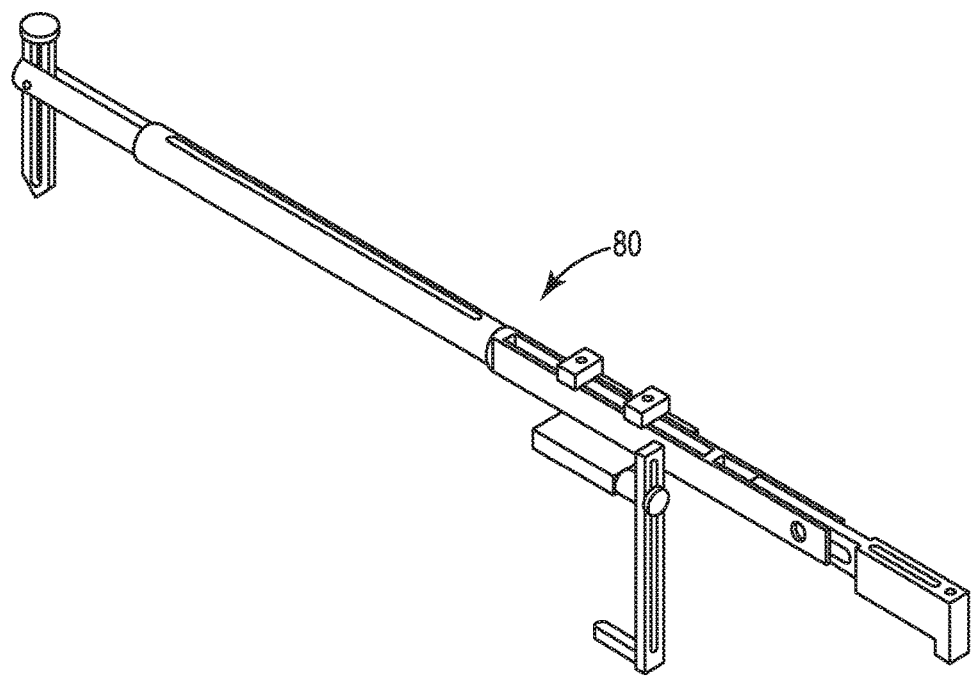
FIG. 7 is a perspective view of a tibial mechanical axis finder.
Figure 8:
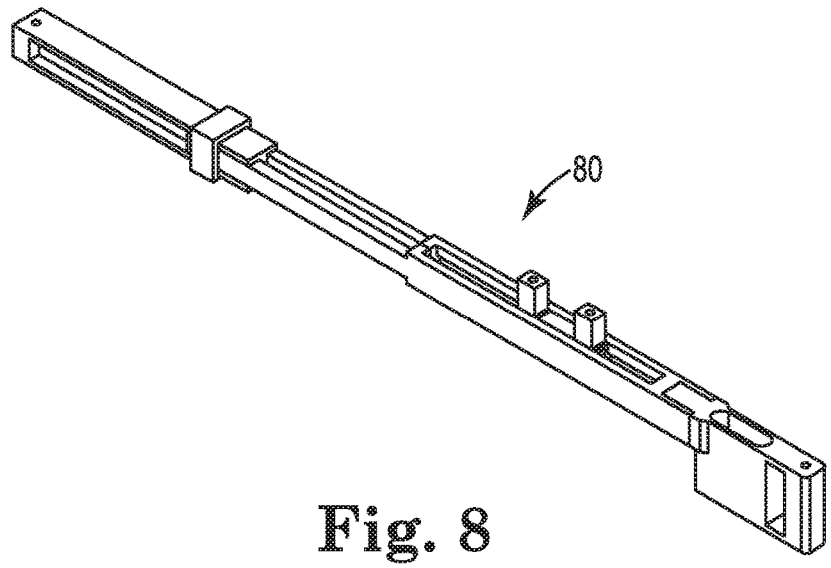
FIG. 8 is another perspective view of a tibial mechanical axis finder.
Figure 9:
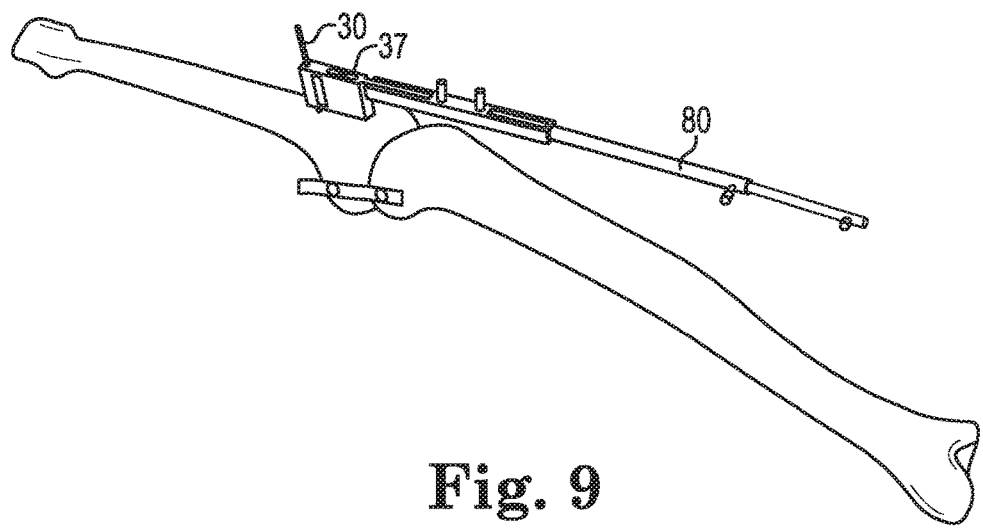
FIG. 9 is a perspective view of a tibial mechanical axis finder positioned relative to a representative tibia and femur.
Figure 10:
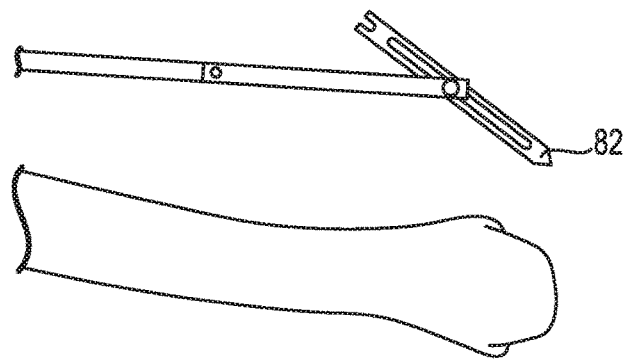
FIG. 10 is a side view of an end portion of a tibial mechanical axis finder with a pointer at its distal end, which is positioned relative to a representative tibia.
Figure 11:
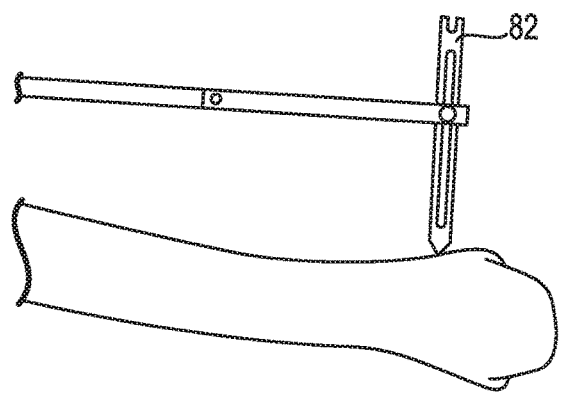
FIG. 11 is another side view of an end portion of a tibial mechanical axis finder with a pointer at its distal end, which is positioned relative to a representative tibia.
Figure 12:
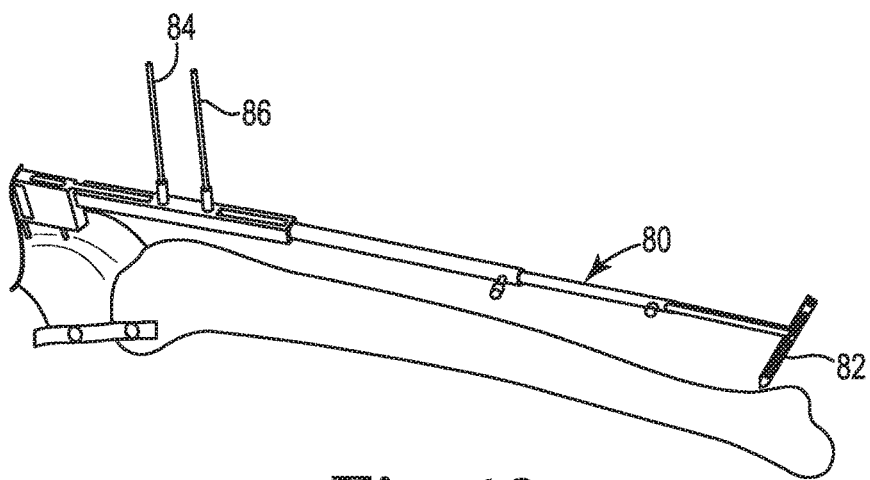
FIG. 12 is a perspective view of a tibial mechanical axis finder with a pointer at its distal end, which is positioned relative to a representative tibia.
Figure 13:
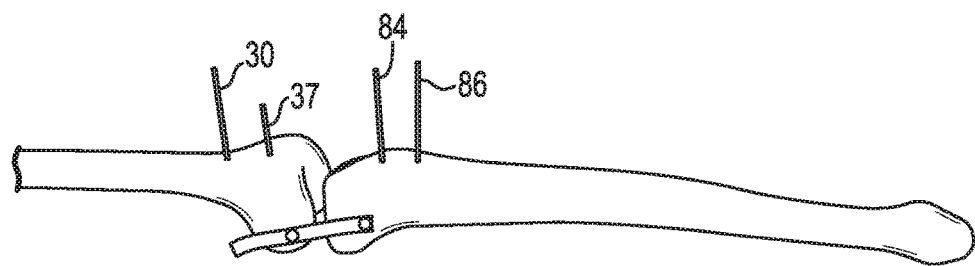
FIG. 13 is a perspective view of a representative tibia and femur with multiple extending pins.

In a next step of the procedure, soft tissue release is performed and the tibial mechanical axis is located, wherein such a procedure can be performed using an exemplary tibial mechanical axis finder 80 of the type illustrated in FIGS. 7 and 8. Steps using such a tibial mechanical axis finder are illustrated in FIGS. 9-13. In particular, the tibial mechanical axis finder 80 is positioned onto the two anterior femoral pins 30, 37 discussed above. In this way, this device will be an extension of the femoral mechanical axis that will form the correct mechanical axis of the whole lower extremity from the center of the femoral head, through the center of the knee, and to the center of the ankle. Appropriate soft tissue releases (e.g., lateral release, etc.) are then performed in the knee to cause the ankle to coincide with the distal tip of the tibial mechanical axis finder, thereby effectively realigning the limb to the correct coronal mechanical axis, which is one basic objective in a good total knee arthroplasty.

The tibial mechanical axis finder 80 may include telescoping members so that its length is adjustable to match the length of the tibia. Further, the tibial mechanical axis finder 80 may also be adjustable along the sagittal plane. That is, the tibial mechanical axis finder 80 is then aligned along the sagittal plane by making it parallel to the palpable fibula or by orienting it at an appropriate angle relative to the anterior aspect of the tibia. A pivotable pointer 82 is downwardly rotatable so that its tip can be used to align the tibial mechanical axis finder 80 to the center of the ankle. Once this is done, two threaded pins 84, 86 are placed through the appropriate guides (see FIG. 12) so that at the end of the process, two pins 84, 86 are properly located on the tibia and two pins 30, 37 are properly located on the femur. In addition, all of the pins are then desirably aligned correctly in their respective coronal and sagittal planes.

Figure 14:
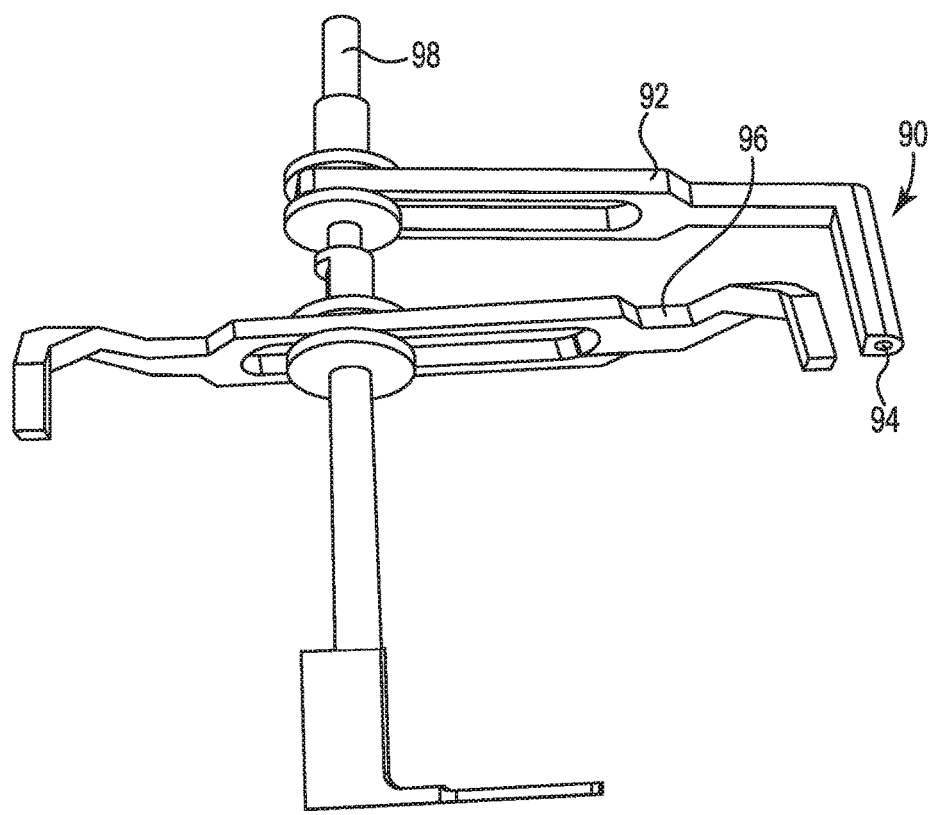
FIG. 14 is a perspective view of a femoral sizer.

Referring now to FIGS. 14-24, the next steps in the procedure include sizing the femur and applying a femoral cutting block to the distal end of the femur. To accomplish this, the knee is placed at approximately 90 degrees of flexion, and a femoral sizer is then placed through the femoral pin. Exemplary embodiments of a femoral sizer 90 are illustrated in FIGS. 14, 16, and 17, with placement of such a sizer 90 relative to a femur illustrated in FIG. 15. Femoral sizer 90 includes a top member 92 having a distal tip 94 and a bottom member 96 that is slidable relative to a post 98 to adjust to the size of the femur. The members 92, 96 are used like calipers, wherein the distal tip 94 of member 92 is engageable with pin 37, for example, to provide the desired reference point for measurement. Alternatively, the sizing step described above can be performed after the femur and tibia are spread apart while in flexion in order to make the collateral ligaments taut and for the femur to rotate and orient properly relative to the tibia. A spreader or "jack-up device" 160, such as the device illustrated in FIG. 29, can be used for this purpose. A size measurement of the femur is then taken in a direction parallel to the tibial mechanical axis.

Figure 18:
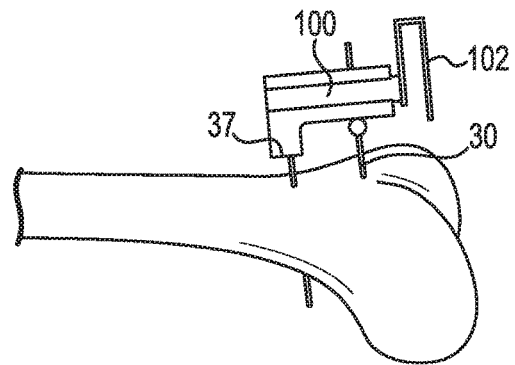
FIG. 18 is a perspective view of a cutting block alignment jig positioned relative to a representative femur.

Once the size of the femur is known, the sizer 90 is removed and replaced by a correspondingly sized femoral cutting block or jig, which is connected to the two anterior femoral pins 30, 37 through the cutting block alignment jig 100 shown in FIG. 18. The cutting block alignment jig 100 allows a cutting block 110 to rotate and translate about a plane perpendicular to the femoral mechanical axis. The block 110 is attachable to the alignment jig 100 via an extending flange 102 onto which a slot of the cutting block 110 can slide.

Figure 19:
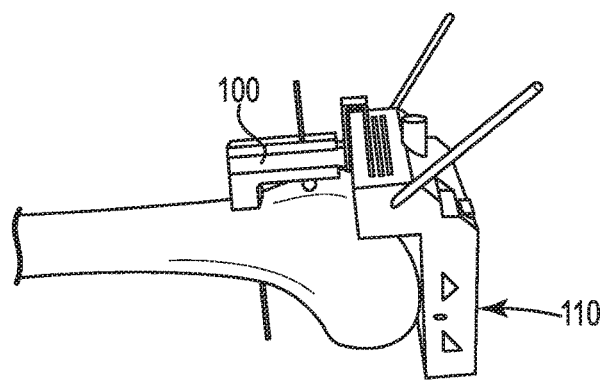
FIG. 19 is a perspective view of a cutting block alignment jig and femoral cutting block positioned relative to a representative femur.
Figure 20:
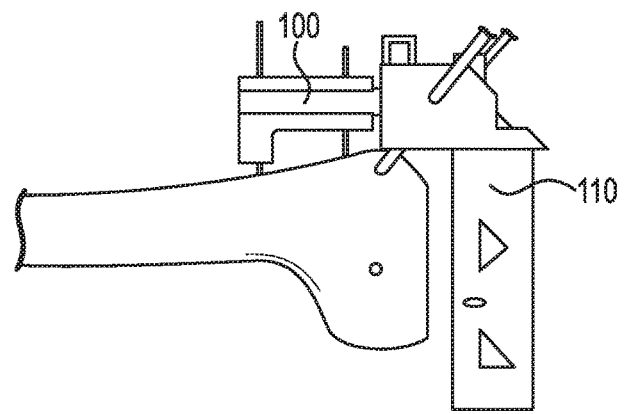
FIG. 20 is a side view of a cut end of a representative femur positioned relative to a cutting block.
Figure 21:
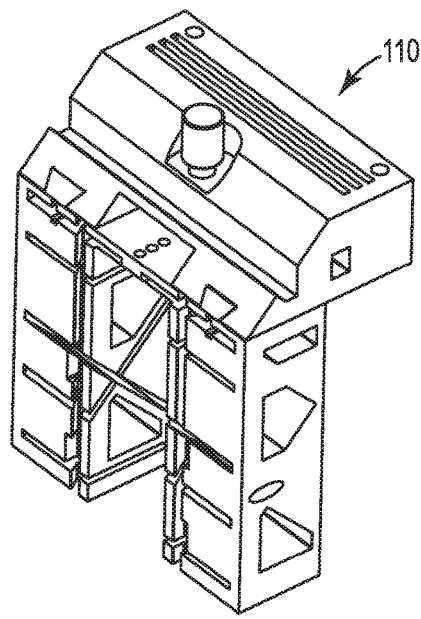
FIG. 21 is a perspective view of an embodiment of a femoral cutting block, in accordance with the invention.
Figure 22:
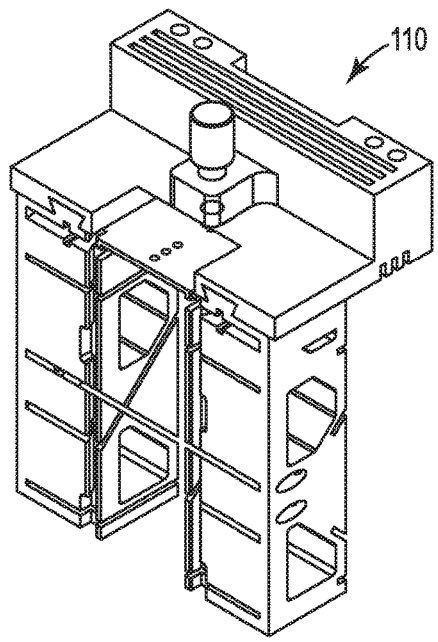
FIG. 22 is a perspective view of an embodiment of a femoral cutting block, in accordance with the invention.
Figure 23:
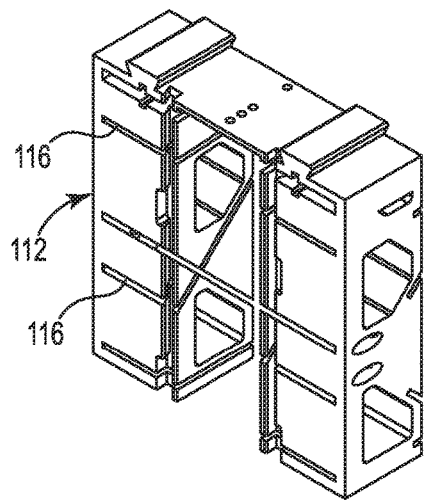
FIG. 23 is a perspective view of a portion of a femoral cutting block, such as of the type illustrated in FIG. 22.
Figure 24:
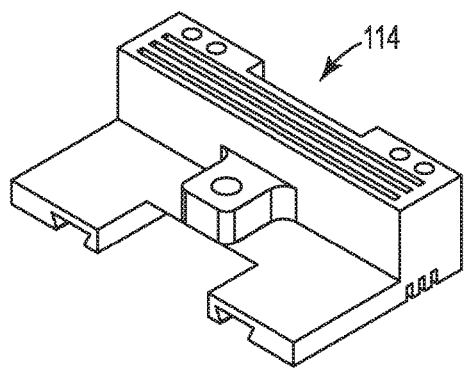
FIG. 24 is a is a perspective view of a portion of a femoral cutting block, such as of the type illustrated in FIG. 22.
Figure 25:
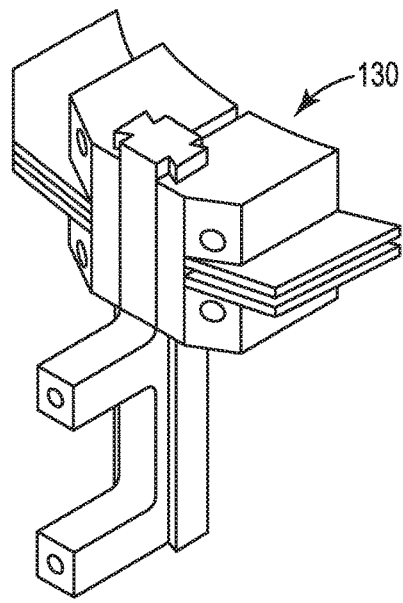
FIG. 25 is a perspective view of a tibial cutting block, according to an embodiment of the invention.

An embodiment of a femoral cutting block that can be used in this procedure is illustrated in FIGS. 19-24 in its assembled and disassembled configurations. In particular, FIGS. 21 and 22 show the cutting block 110 in an assembled condition, while FIGS. 23 and 24 illustrate separate block pieces 112 and 114 of the block 110, respectively. Block piece 112 includes multiple slots 116 into which cutting blades can be inserted to cut the bone at desired locations when the block is in certain, predetermined locations relative to the femur. FIG. 19 shows the position of the cutting block 110 when attached to the cutting block alignment jig 100. When the cutting block 110 is positioned in this manner, the block will be in the correct varus-valgus angle (coronal plane) and the correct flexion-extension angle (sagittal plane) with respect to the femur.

After the cutting block 110 is properly positioned, the distal femur is cut using a cutting blade that is pressed through a predetermined slot 116 of the cutting block 110. FIG. 20 shows the femur with the distal end removed by the cutting process. The cutting block 110 is then advanced or collapsed proximally so that the cutting block 110 is in contact with the cut surface of the femur. This cut of the femur can be a single distal cut, which is made prior to the other cuts in order for the femoral cutting block 110 to be collapsed for the succeeding cuts. The distal cut can also be done together with all the other cuts without collapsing the cutting block 110 (with a corresponding modification in the cutting block); however, the cutting block 110 can be more stable if it is flush against the flat distal cut surface of the femur and then pinned in place, instead of abutting against the generally round profile of the natural distal condyle.

Figure 26:
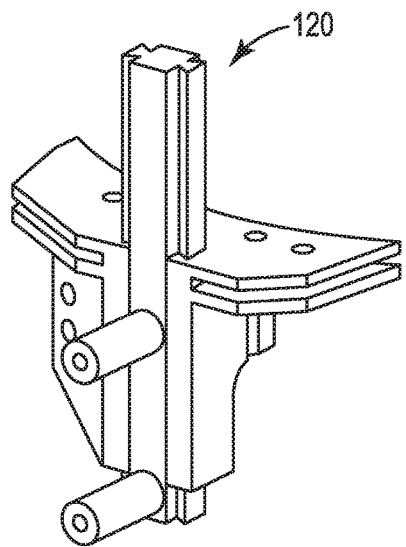
FIG. 26 is a perspective view of a tibial cutting jig, according to an embodiment of the invention.
Figure 27:
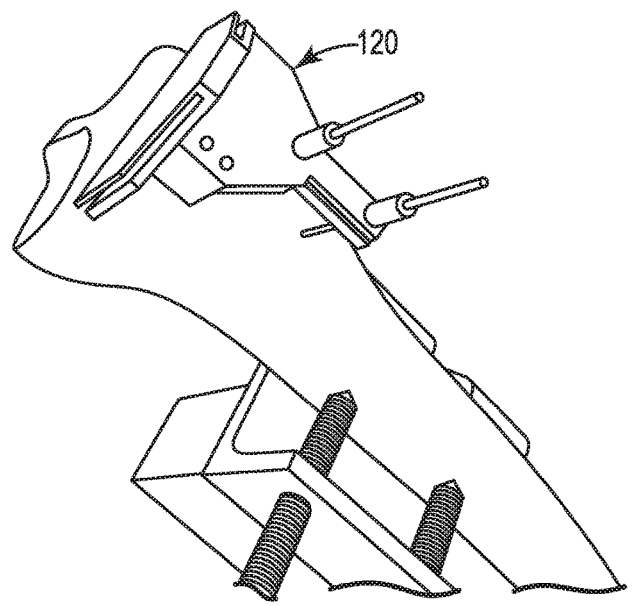
FIG. 27 is a perspective view of a tibial cutting jig positioned relative to an end of a representative tibia.

Next, a tibial cutting jig 120, shown in FIGS. 26 and 27, is slid onto the two pins 84, 86 that were previously placed in the tibia. The tibial cutting block 130 can then be positioned relative to the tibial cutting jig 120. This positions the block 130 in the correct varus-valgus angle (coronal plane) and correct flexion-extension angle (sagittal plane) with respect to the tibia.

Figure 28:
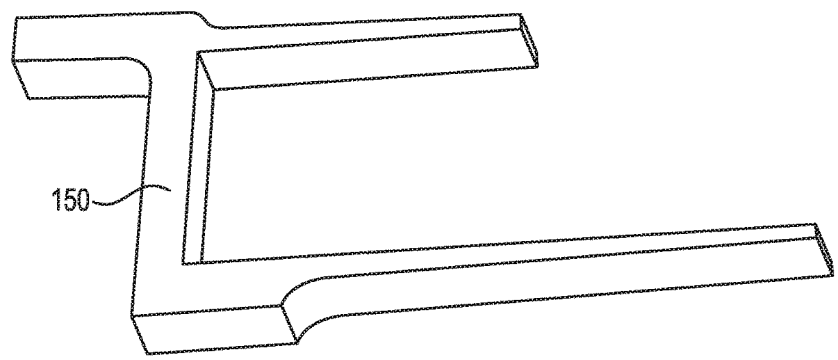
FIG. 28 is a perspective view of a C-clip, according to an embodiment of the invention.

As described herein, previous systems that are known in the art will involve cutting of the tibia and the femur separately, and then attempt to relate or match the two bones after the bone cuts have been made. In accordance with the present invention, however, the total knee arthroplasty systems and methods will match the bones prior to making the bone cuts. A number of components are used for this process, including at least one of an anterior reference guide "scorpion tail" (illustrated in FIGS. 32 and 33), a C-clip (illustrated in FIG. 28), and a spreader (illustrated in FIG. 29), which components are described in further detail below.

Figure 30:
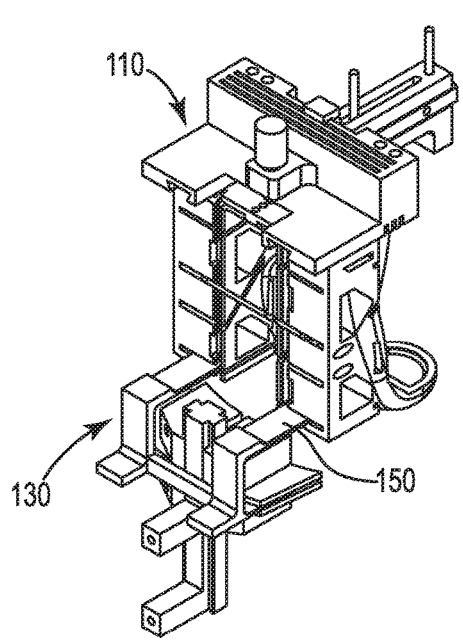
FIG. 30 is a perspective view of a tibial cutting block and femoral cutting block.
Figure 31:
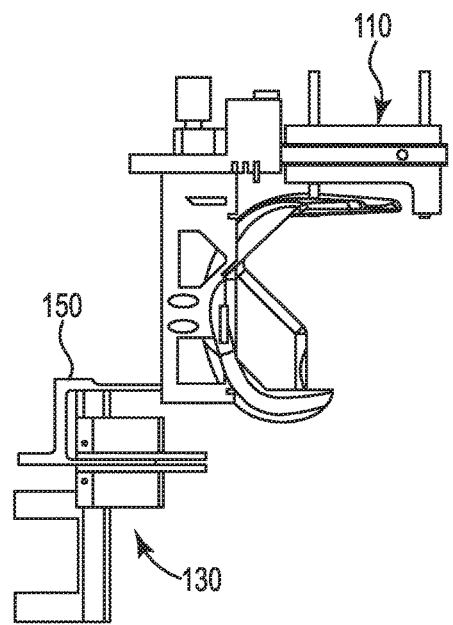
FIG. 31 is a side view of a tibial cutting block and femoral cutting block.
Figure 32:
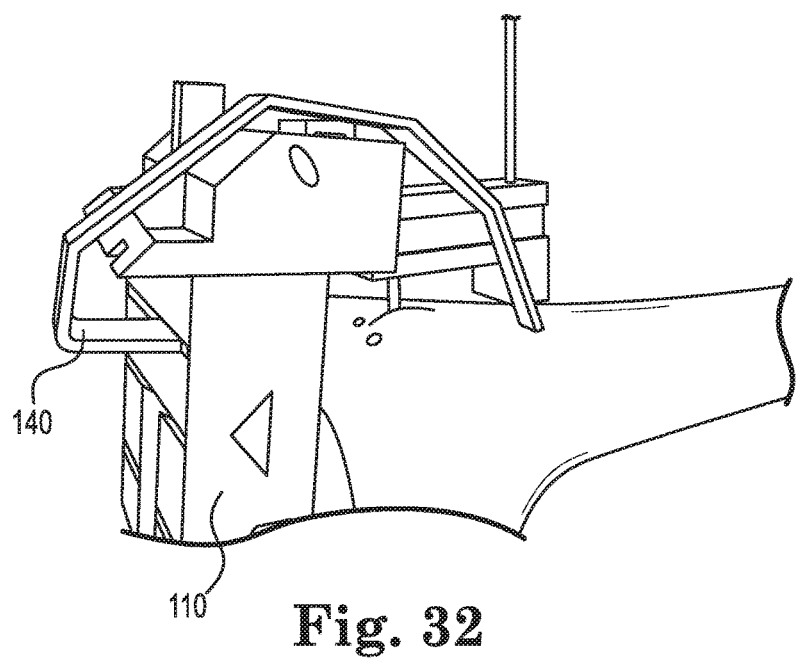
FIG. 32 is a perspective view of a femoral cutting block with a scorpion tail attachment of the invention.
Figure 33:
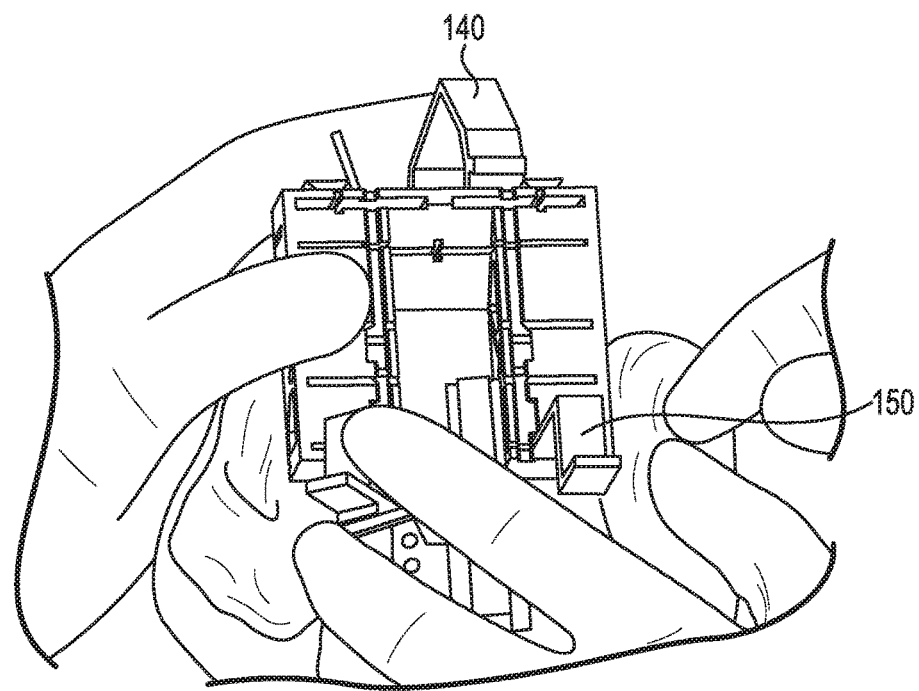
FIG. 33 is another perspective view of a femoral cutting block with a scorpion tail attachment of the invention, and positioned relative to a knee.

In particular, FIGS. 32 and 33 illustrate an attachment referred to herein as a "scorpion tail" 140, which is attachable to the femoral cutting block 110 for positioning that block along the antero-posterior direction relative to the anterior femoral cortex. The scorpion tail attachment 140 defines the anterior cut and also prevents notching of the anterior femoral cortex. A C-clip 150 is then applied to connect the femoral cutting block and the tibial cutting block (i.e., to match the femur and the tibia so that they are parallel), such as is illustrated in FIGS. 30 and 31. While one embodiment of C-clip 150 is illustrated herein, it is understood that a surgeon may be provided with a number of C-clips from which he can choose for each particular patient. The C-clip 150 defines the flexion gap and positions the tibial cutting block 130 so only the required amount of tibial plateau is cut. Thus, the C-clip 150 also determines the thickness of the tibial implant component to be used. The C-clip 150 can come in various gap sizes corresponding to the different tibial implant component thicknesses.

Figure 29:
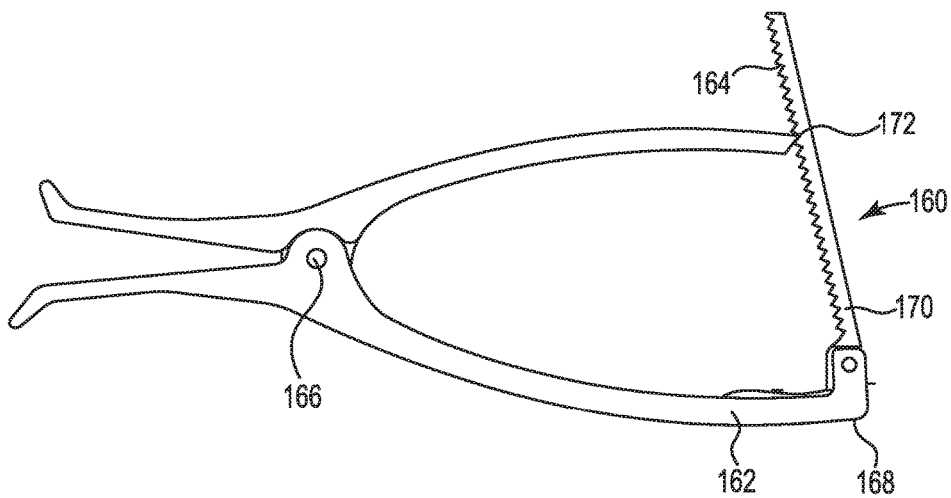
FIG. 29 is a side view of a spreader, according to an embodiment of the invention.
Figure 34:
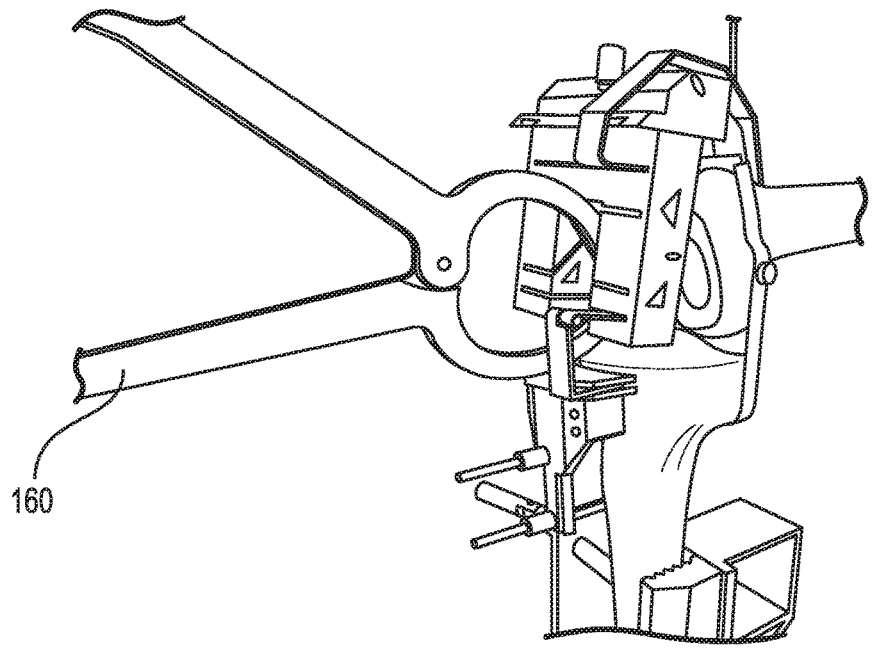
FIG. 34 is a perspective view of various components of the total knee arthroplasty devices used in accordance with the invention, including a spreader.

A spreader or "jack-up device" 160, such as the device illustrated in FIG. 29, is then positioned between the tibial spine and the intercondylar notch. The spreader 160 includes first and second arms 162, 164 pivotably connected to each other at pivot point 166. Distal end 168 of arm 162 includes an extending ratchet member 170 that is engageable with a distal end 172 of arm 164, which provides the desired spreading function to the device. Notably, none of the cutting blocks need to be removed to place this spreader 160 in its desired location. The handles or proximal ends of arms 162, 164 are squeezed toward each other, to rotate the femur to the correct angle due to the tensioning of both the collateral ligaments, as is illustrated in FIG. 34, for example. In this case, the adjustment is accomplished using spreader 160 that includes ratcheting member 170 to lock the arms 162, 164 in place relative to each other and cause the femur to rotate, orienting the femoral cutting block in the correct rotation relative to the femur.

It can be noted that during this spreading step, the femoral cutting block is held parallel to the tibial cutting block by the C-clip 150. At the same time, it is held perpendicular to the femoral mechanical axis by the cutting block alignment jig of FIG. 18. This adjustment provides more individualized adjustment for each patient, rather than using a fixed amount of rotation, as is assumed in other systems (e.g., 3-5 degrees of rotation). Correct femoral rotation allows for a more balanced flexion gap, better range of motion and better patellar tracking. Once the correct positions of the femoral cutting block 110 and the tibial cutting block 130 are established, both are stabilized using pins. The scorpion tail attachment 140, spreader 160, and the C-clip 150 are then removed.

Figure 35:
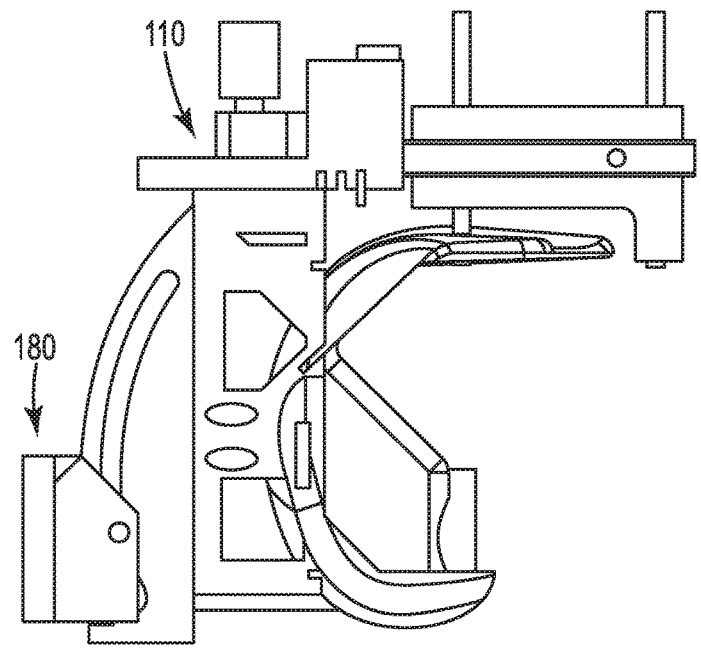
FIG. 35 is a side view of a femoral cutting block and a box reamer in a first position.
Figure 36:
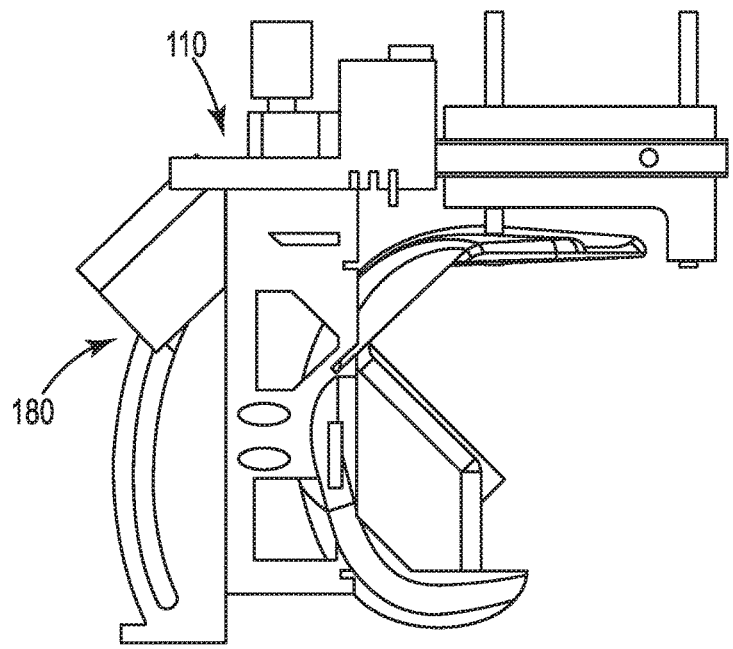
FIG. 36 is a side view of a femoral cutting block and a box reamer in a second position.
Figure 37:
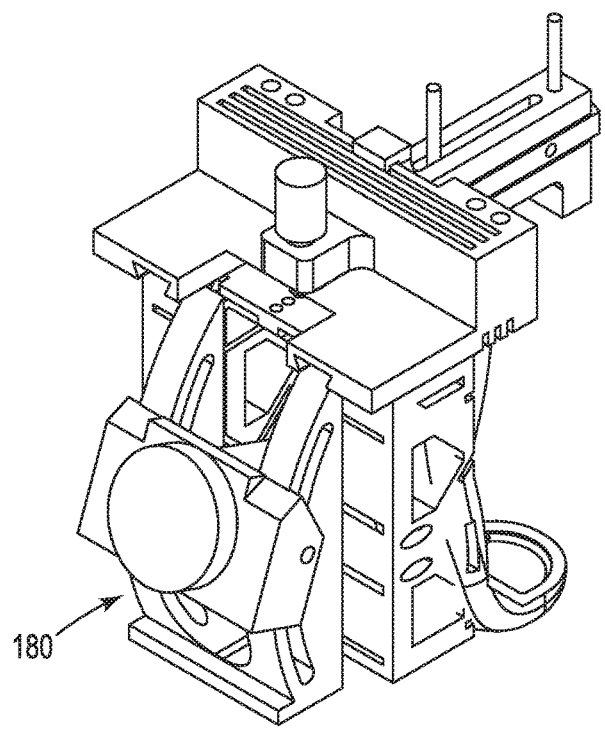
FIG. 37 is a perspective view of a femoral cutting block and box reamer.
Figure 38:
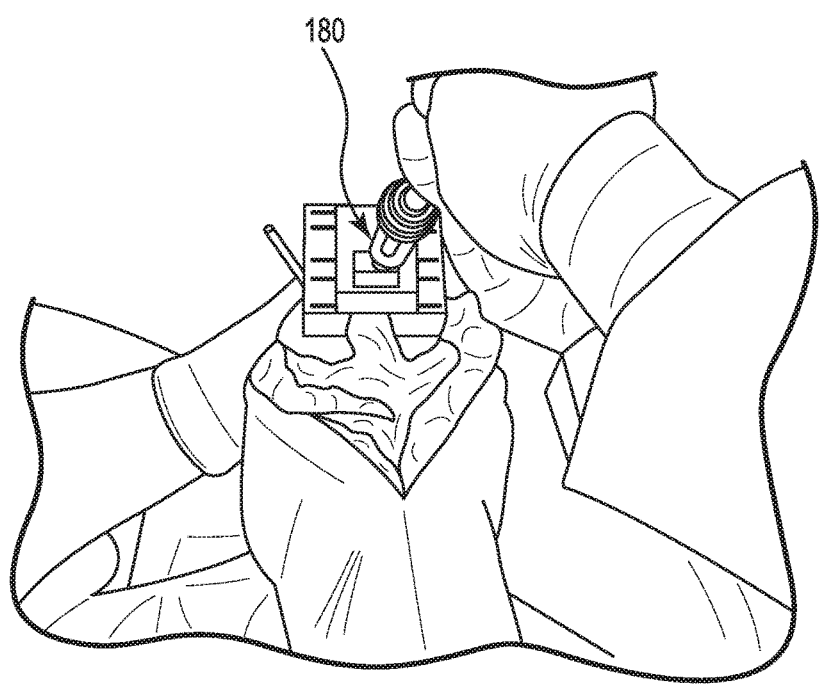
FIG. 38 is another a perspective view of a femoral cutting block and box reamer.
Figure 39:
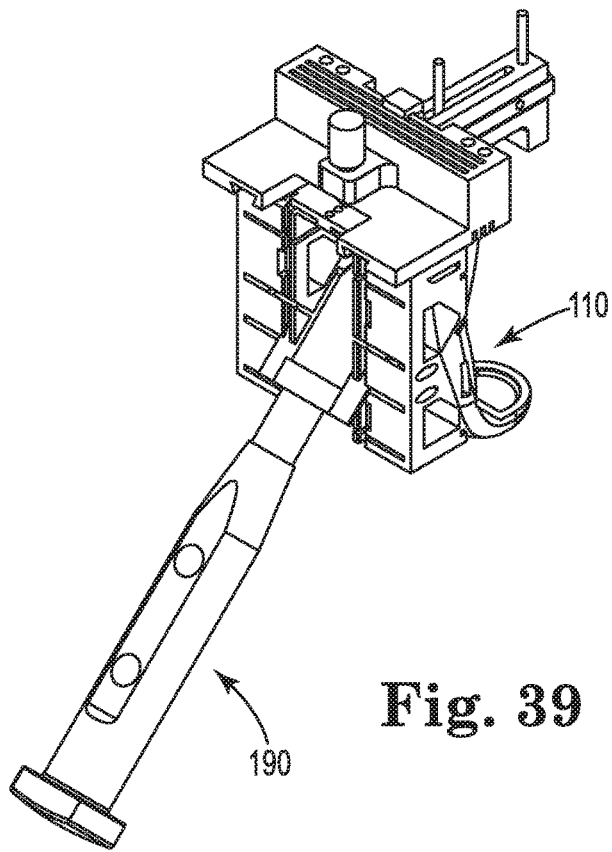
FIG. 39 is a perspective view of a chisel positioned relative to a femoral cutting block.

At this point, the cutting jigs or blocks will be in their desired positions relative to their respective bones. As discussed above, using an oscillating saw, the distal femur is cut, then the femoral cutting block is advanced onto the cut surface. Guides (i.e., slots 116) of the cutting block 110 are then used for making the following cuts: the anterior femur cut, the anterior chamfer, the posterior cut, and the posterior chamfer. In one embodiment, the "roof" or proximal surface of the box and the distal femur are cut first, and then the cutting block is pushed or collapsed onto the cut distal femur and it is pinned in place. A device that is referred to herein as a "box reamer" is then used to make a box cut, wherein an embodiment of a box reamer 180 is illustrated in FIGS. 35-37, and is shown relative to the femoral cutting block in FIG. 38. Alternatively, an oscillating saw can be used to cut the side of the box. Another alternative is to use a box chisel or similar tool to cut out the box. In an alternative sequence of cutting steps, the box is cut after the distal femur is cut. The anterior and posterior chamfers can be cut before or after their respective anterior and posterior cuts, as desired. The tibia is then cut, using the tibia cutting block as a guide. A chisel 190 of the type illustrated in FIG. 39 can then be used to cut the "hump" for the implant, wherein an exemplary positioning of the chisel 190 relative to the femoral cutting block 110 is also shown. Alternatively, a bone rasp with the appropriate profile can be used to cut the "hump".

Next, the cutting jigs or blocks are removed, and a tibial drill guide is positioned and pinned in place, and the tibial reference pins are removed. The tibia is then drilled, and then the tibial drill guide is removed. A trial tibial base plate is then applied to the cut portion of the bone.

Figure 40:
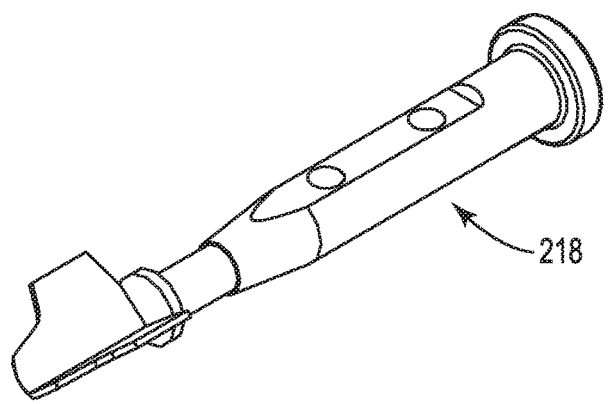
FIG. 40 is a perspective view of a tibial fin punch.
Figure 41:
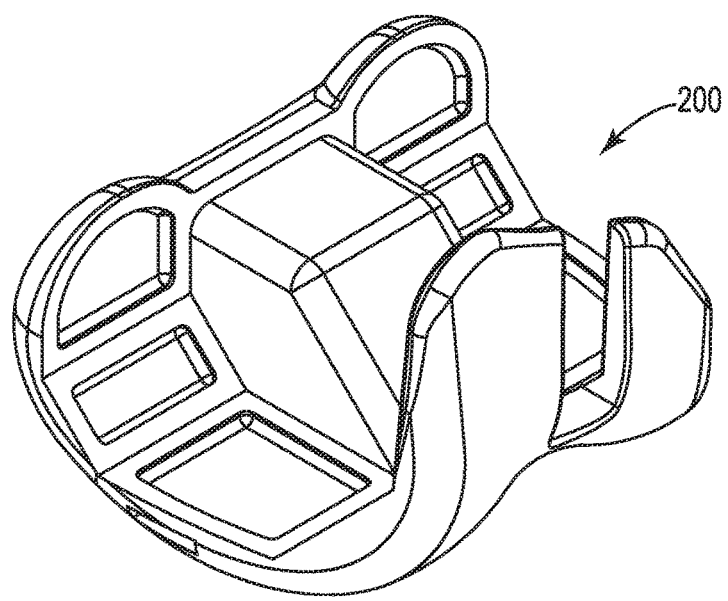
FIG. 41 is a perspective view of a trial femoral component.
Figure 42:
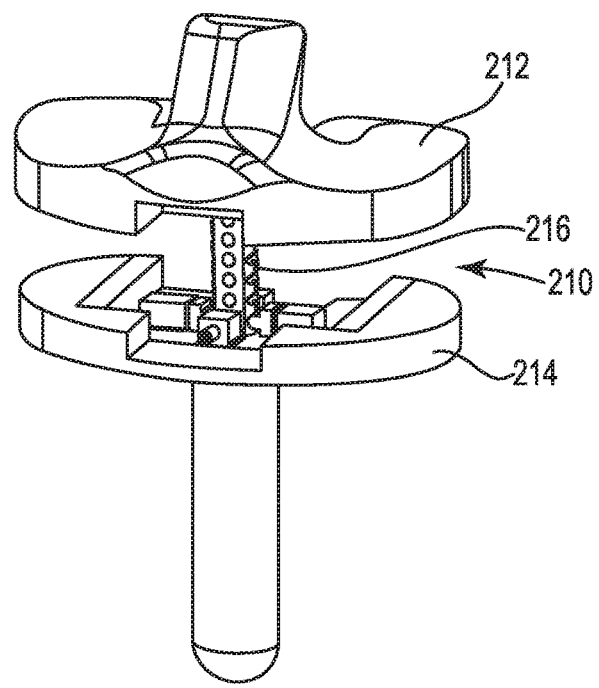
FIG. 42 is a perspective view of a trial tibial insert.

Posterior osteophytes, if any, are removed, and then a femoral trial component is placed on the distal femur, which component has been selected to be the correct size for the particular patient. An exemplary trial femoral component 200 is illustrated in FIG. 41. A corresponding correct size tibial trial insert is applied on the proximal tibia with the correct thickness setting of the insert, as determined by the C-clip size used above. The trial component thickness can be increased without removing it from the knee by using an adjustable trial tibial insert 210, of the type that is illustrated in FIG. 42, for example. Trial tibial insert 210 includes an upper piece 212 that is adjustable relative to a lower piece 214 along a post 216. Movement of the pieces 212, 214 until they are positioned at a desired distance from each other will correspond with the thickness needed for the final tibial component. Alternatively, trial tibial components with fixed thicknesses can be used. Assessments are then made as to the knee's ability to achieve a stable full extension and a stable flexion with good patellar tracking. Alignment is confirmed by a rod applied on the pins, which will go from the center of the femoral head through the center of the knee to the center of the ankle. Additional releases and balancing can then be performed. In addition, the tibial plate rotation can be marked, and a tibia fin punch 218 (see FIG. 40, for example) can be used to punch an appropriate opening in the tibia. Finally, the trial components can be removed and replaced with the final implant components, which are then cemented into place.

If it is desired to resurface the patella, the following procedure and corresponding instrumentation can be used in accordance with the invention. First, the thickness of the patella is measured, which may be accomplished by first everting the patella and then placing it in a patellar clamp 220, such as is shown in FIG. 43, to establish the plane along which the patella is cut. The thickness of the patella can then be measured with a device such as a caliper, for example. However, due to the irregular shape of the patella, the line connecting the points on the surface of the patella corresponding to its thickness may not be perpendicular to the cutting surface. In such a case, it may be difficult to properly orient the caliper in order to make an accurate measurement. Therefore, in accordance with the invention, the thickness of the patella can be measured using a measuring sleeve 222 (shown in FIG. 45) attached to a reamer shaft 224 with graduations (shown in FIG. 44). The reamer shaft 224 and measuring sleeve assembly 230 (shown in FIG. 45) are then inserted into the patellar clamp. An indicator sleeve is used to measure the thickness of the patella using the graduations on the reamer shaft, as is shown in FIG. 46.

Figure 47:
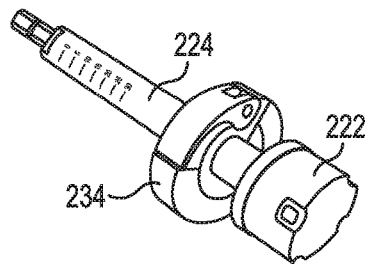
FIG. 47 is a perspective view of a reamer shaft with an attached shaft collar.
Figure 48:
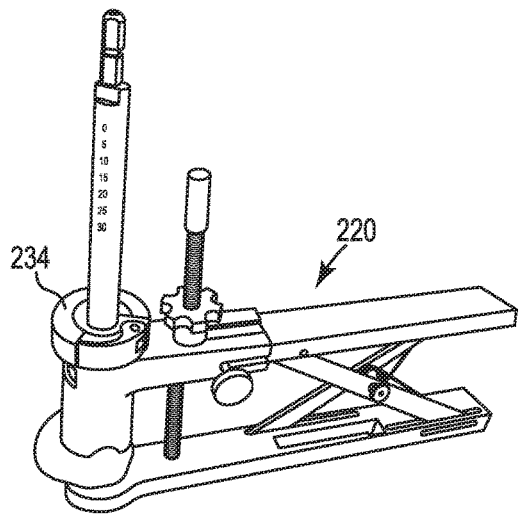
FIG. 48 is a perspective view of the reamer shaft and attached collar of FIG. 47 positioned relative to a patellar clamp.
Figure 49:
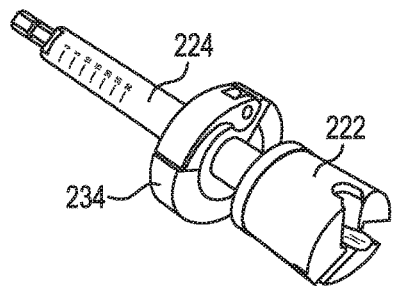
FIG. 49 is a perspective view of a reamer shaft having a reamer at one end.
Figure 50:
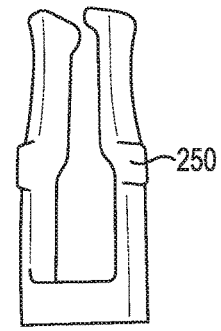
FIG. 50 is a perspective view of a cement clamp.
Figure 51:
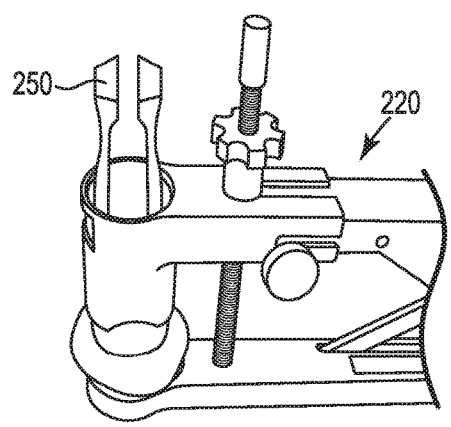
FIG. 51 is a perspective view of the cement clamp positioned relative to a patellar clamp.

After measuring the thickness of the patella, a shaft collar 234 is placed over the reamer shaft 224, as is shown in FIG. 47. The shaft collar 234 is pressed flush on the patellar clamp 220 and locked in place, as is shown in FIG. 48. The shaft collar 234 acts as a stopper to prevent over-reaming and ensure that the patella is reamed to the proper depth. The measuring sleeve 222 is then removed and replaced with a reamer 240 as shown in FIG. 49. The patella is then reamed until the shaft collar abuts against the top surface of the patellar clamp. A trial patellar implant can be used to verify the fit of the patellar implant. The patellar implant is then cemented into place. A cement clamp 250 such as the type shown in FIG. 50 can be attached to the patellar clamp 220 to hold the patellar implant in place while the cement is curing, as is illustrated in FIG. 51.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described herein and the equivalents of those structures.

The invention claimed is:

1. A method of performing a total knee arthroplasty comprising:
    exposing bones of a knee of a patient;
    identifying a positional center of the knee using a knee center locator device;
    inserting a first pin into an anterior aspect of a distal femur and through the center of the knee;
    locating a femoral mechanical axis with reference to the center of the knee using a mechanical axis finder;
    inserting at least one additional pin into the anterior aspect of the distal femur, the axis of said at least one additional pin intersecting with and perpendicular to the femoral mechanical axis;
    locating a tibial mechanical axis using a tibial mechanical axis finder;
    sizing the femur using a femoral sizer positioned on at least one of the pins inserted into the femur;
    applying a femoral cutting block to a distal end of the femur, wherein the femoral cutting block comprises at least one femoral cutting guide;
    positioning a tibial cutting block in a cutting position relative to a proximal end of the tibia, wherein the tibial cutting block comprises at least one tibial cutting guide;
    aligning the femoral cutting block relative to the tibial cutting block;
    aligning the femur relative to the tibia;

cutting the femur through the at least one femoral cutting guide;
cutting the tibia through the at least one tibial cutting guide;
removing the femoral and tibial cutting blocks; and
positioning a permanent femoral knee implant component on the cut portion of the femur and positioning a permanent tibial knee implant component on the cut portion of the tibia.

2. The method of claim 1, wherein the femoral and tibial cutting guides each comprise slots through the femoral and tibial cutting blocks, respectively.

3. The method of claim 2, wherein the cutting guides of each of the femoral and tibial cutting blocks are positioned in locations that allow for all of the cuts to be performed on the femur and tibia that are desired for accepting their respective permanent knee implant components.

4. The method of claim 1, wherein the step of aligning the tibia relative to the femur comprises positioning a jack-up device between a tibial spine and an intercondylar notch and activating the jack-up device to orient the femur in a desired external and internal rotation relative to the tibia while the femoral and tibial cutting blocks are attached to each other.

5. The method of claim 4, wherein the jack-up device comprises a first arm pivotable relative to a second arm about a pivot point, and wherein activation of the jack-up device comprises moving the first and second arms relative each other about the pivot point to move distal ends of the first and second arms relative to each other.

6. The method of claim 4, wherein the femoral and tibial cutting blocks remain in their respective rotational positions relative to each other during the positioning and activating of the jack-up device.

7. The method of claim 1, wherein the mechanical axis finder does not require violation of the intramedullary canal of the femur.

8. The method of claim 1, wherein the step of locating the femoral mechanical axis comprises the steps of:
identifying a representative sphere traced by a trace point offset by a predetermined distance from the center of the knee, wherein a center of the representative sphere is coincident with a center of a femoral head;
identifying at least three points on the representative sphere;
locating the center of a circle defined by the at least three points on the representative sphere;
identifying a line passing through the center of, and perpendicular to the plane of, the circle defined by the at least three points on the representative sphere;
positioning the femur such that a line connecting the center of the femoral head and the trace point is coincident with the line passing through the center of, and perpendicular to the plane of, the circle defined by the at least three points on the representative sphere; and
placing a plurality of pins on the femur to identify the location of the femoral mechanical axis in both the coronal and sagittal planes, such pins being positioned on the femur in such a way as to compensate for the predetermined offset of the trace point from the center of the knee so that the line connecting the center of the femoral head and the trace point has a predetermined angular offset from the femoral mechanical axis.

9. The method of claim 1, further comprising the step of resurfacing the patella of the patient after positioning the permanent femoral and tibial knee implant components relative to the femur and tibia, respectively.

10. The method of claim 1, wherein after the step of removing the femoral and tibial cutting blocks, the method further comprises the step of positioning at least one trial femoral knee implant component and at least one trial tibial knee implant component on the cut portion of the femur and the cut portion of the tibia, respectively, and then removing the trial femoral and tibial knee implant components prior to the step of positioning permanent femoral and tibial knee implant components.

11. The method of claim 1, wherein prior to the step of positioning permanent femoral and tibial knee implant components, the method further comprises checking the leg alignment using a rod placed on the first pin and the at least one additional pin inserted into the anterior aspect of the femur in alignment with the femoral mechanical axis.

12. The method of claim 1, wherein the step of aligning the tibia relative to the femur comprises balancing and rotationally orienting the tibia and femur, and determining the thickness of at least one insert.

13. The method of claim 1, further comprising the step of performing soft tissue release to align the tibial mechanical axis with the femoral mechanical axis after the step of locating the tibial mechanical axis and before the step of cutting the femur and the step of cutting the tibia.

14. The method of claim 1, wherein the step of locating the tibial mechanical axis comprises aligning a tibial mechanical axis finder along a sagittal plane of the tibia and placing first and second tibial pins in the tibia using guides of tibial mechanical axis finder.

15. The method of claim 1, wherein the step of positioning a tibial cutting block in a cutting position relative to the tibia comprises attaching a tibial cutting jig to the first and second tibial pins and attaching the tibial cutting block to the tibial cutting jig.

16. The method of claim 1, wherein the femoral cutting block comprises a removably attachable scorpion tail member used for positioning the femoral cutting block in an antero-posterior direction relative to an anterior femoral cortex in the step of aligning the femoral cutting block relative to the tibial cutting block.

17. The method of claim 1, wherein the step of aligning the femoral cutting block relative to the tibial cutting block comprises attaching the femoral cutting block to the tibial cutting block.

18. The method of claim 17, wherein the step of attaching the femoral cutting block to the tibial cutting block comprises attaching a clip member to the femoral and tibial cutting blocks.

19. The method of claim 1, wherein prior to the step of sizing the femur, the method further comprises the step of positioning a jack-up device between a tibial spine and an intercondylar notch and activating the jack-up device to orient the femur in a desired external and internal rotation relative to the tibia, and wherein the step of sizing the femur is performed by measuring the femur parallel to the tibial mechanical axis in 90 degrees of flexion.

20. A method of performing a total knee arthroplasty comprising:
exposing bones of a knee of a patient;
identifying a positional center of the knee using a knee center locator device;
inserting a first pin into an anterior aspect of a distal femur and through the center of the knee;
locating a femoral mechanical axis with reference to the center of the knee using a mechanical axis finder, wherein the step of locating the femoral mechanical axis comprises the steps of:

identifying a representative sphere traced by a trace point offset by a predetermined distance from the center of the knee, wherein a center of the representative sphere is coincident with a center of a femoral head;

identifying at least three points on the representative sphere;

locating the center of a circle defined by the at least three points on the representative sphere;

identifying a line passing through the center of, and perpendicular to the plane of, the circle defined by the at least three points on the representative sphere;

positioning the femur such that a line connecting the center of the femoral head and the trace point is coincident with the line passing through the center of, and perpendicular to the plane of, the circle defined by the at least three points on the representative sphere; and placing a plurality of pins on the femur to identify the location of the femoral mechanical axis in both the coronal and sagittal planes, such pins being positioned on the femur in such a way as to compensate for the predetermined offset of the trace point from the center of the knee so that the line connecting the center of the femoral head and the trace point has a predetermined angular offset from the femoral mechanical axis;

inserting at least one additional pin into the anterior aspect of the distal femur, the axis of said at least one additional pin intersecting with and perpendicular to the femoral mechanical axis;

locating a tibial mechanical axis using a tibial mechanical axis finder;

sizing the femur using a femoral sizer positioned on at least one of the pins inserted into the femur;

sizing the femur and applying a femoral cutting block to a distal end of the femur, wherein the femoral cutting block comprises at least one femoral cutting guide;

positioning a tibial cutting block in a cutting position relative to a proximal end of the tibia, wherein the tibial cutting block comprises at least one tibial cutting guide;

aligning the femoral cutting block relative to the tibial cutting block;

aligning the femur relative to the tibia;

cutting the femur through the at least one femoral cutting guide;

cutting the tibia through the at least one tibial cutting guide;

removing the femoral and tibial cutting blocks; and positioning a permanent femoral knee implant component on the cut portion of the femur and positioning a permanent tibial knee implant component on the cut portion of the tibia.

* * * * *